(12) United States Patent
Vidal Vieira et al.

(10) Patent No.: US 9,347,021 B2
(45) Date of Patent: May 24, 2016

(54) PROCESS FOR THE PRODUCTION OF AVIATION BIOKEROSENE AND AVIATION KEROSENE COMPOSITION

(75) Inventors: Jose Antonio Vidal Vieira, Rio de Janeiro (BR); Mauro Iurk Rocha, Niteroi (BR); Roberto Lopes Carvalho, Rio de Janeiro (BR); Marcelo Vieira Alves, Rio de Janeiro (BR)

(73) Assignee: PETROLEO BRASILEIRO S.A.—PETROBRAS, Rio de Janeiro (BR)

( * ) Notice: Subject to any disclaimer, the term of this patent is extended or adjusted under 35 U.S.C. 154(b) by 98 days.

(21) Appl. No.: 13/641,596

(22) PCT Filed: Apr. 7, 2011

(86) PCT No.: PCT/BR2011/000095
§ 371 (c)(1),
(2), (4) Date: Oct. 16, 2012

(87) PCT Pub. No.: WO2011/143728
PCT Pub. Date: Nov. 24, 2011

(65) Prior Publication Data
US 2013/0055624 A1  Mar. 7, 2013

(30) Foreign Application Priority Data

May 21, 2010 (BR) ...................... 1001608

(51) Int. Cl.
| | | |
|---|---|---|
| *C10L 1/19* | (2006.01) | |
| *C11B 3/12* | (2006.01) | |
| *C10L 1/02* | (2006.01) | |
| *C10L 1/04* | (2006.01) | |
| *C11C 3/00* | (2006.01) | |
| *C07C 67/03* | (2006.01) | |

(52) U.S. Cl.
CPC . *C11B 3/12* (2013.01); *C07C 67/03* (2013.01); *C10L 1/02* (2013.01); *C10L 1/026* (2013.01); *C10L 1/04* (2013.01); *C10L 1/19* (2013.01); *C11C 3/003* (2013.01); *C10G 2300/1014* (2013.01); *C10G 2300/1051* (2013.01); *C10G 2300/30* (2013.01); *C10G 2400/08* (2013.01); *C10L 2200/043* (2013.01); *C10L 2200/0476* (2013.01); *C10L 2270/04* (2013.01); *Y02E 50/13* (2013.01); *Y02P 30/20* (2015.11); *Y02T 50/678* (2013.01)

(58) Field of Classification Search
USPC .......................... 585/240; 44/307, 308, 388
See application file for complete search history.

(56) References Cited

U.S. PATENT DOCUMENTS

| | | | | |
|---|---|---|---|---|
| 7,850,745 | B2 * | 12/2010 | Reaney et al. ................. | 44/389 |
| 8,017,819 | B2 * | 9/2011 | Yao et al. ....................... | 585/240 |
| 8,039,682 | B2 * | 10/2011 | McCall et al. ................. | 585/240 |
| 8,058,492 | B2 * | 11/2011 | Anumakonda et al. ......... | 585/14 |
| 8,067,657 | B2 * | 11/2011 | Duarte Santiago et al. .. | 585/733 |
| 8,137,555 | B2 * | 3/2012 | Kale .............................. | 210/601 |
| 8,137,558 | B2 * | 3/2012 | Kale .............................. | 210/634 |
| 8,152,870 | B2 * | 4/2012 | Kale .............................. | 44/385 |
| 8,304,591 | B2 * | 11/2012 | Aulich et al. ................. | 585/240 |
| 8,329,968 | B2 * | 12/2012 | Brandvold et al. ............ | 585/240 |
| 8,329,970 | B2 * | 12/2012 | Harlin et al. ................. | 585/240 |
| 8,741,145 | B2 * | 6/2014 | Kale .............................. | 210/634 |
| 8,742,183 | B2 * | 6/2014 | McCall et al. ................. | 44/308 |
| 2008/0092436 | A1 * | 4/2008 | Seames et al. ................. | 44/308 |
| 2009/0031618 | A1 * | 2/2009 | Morgan ........................ | 44/308 |
| 2010/0151112 | A1 * | 6/2010 | Franklin et al. ............... | 426/656 |
| 2012/0021366 | A1 * | 1/2012 | Moller et al. ................. | 431/320 |

* cited by examiner

*Primary Examiner* — Ellen McAvoy
(74) *Attorney, Agent, or Firm* — Sughrue Mion, PLLC

(57) ABSTRACT

The present invention relates to a process of obtainment of aviation biokerosene and a composition of aviation kerosene containing the aviation biokerosene thus produced. The process consists of simultaneously combining three basic conditions: raw material selection, processing conditions, and control of specific properties of the product. The composition is classified as a semisynthetic composition of aviation kerosene and may contain up to 20% by weight of aviation biokerosene, satisfying the limits determined in the international specifications for aviation kerosene.

7 Claims, No Drawings

PROCESS FOR THE PRODUCTION OF AVIATION BIOKEROSENE AND AVIATION KEROSENE COMPOSITION

FIELD OF THE INVENTION

The present invention relates to a process for the production of aviation biokerosene (BioQAV) from alkyl esters of fatty acids originating from selected renewable raw materials, and an aviation kerosene (QAV) composition containing the aviation biokerosene (BioQAV) thus produced.

BACKGROUND OF THE INVENTION

The necessity for reducing dependency on petroleum, increasingly more scarce and expensive, allied to growing worldwide concern to stop the rise in the temperature of the planet, is leading humanity to take a series of steps in terms of utilising other types of fuels which permit controlling the emission of gases causing the greenhouse effect, without allowing this to negatively affect the development of our industry.

Burning fossil fuels is one of the principal sources of generation of $CO_2$, considered to be most responsible for aggravation of the greenhouse effect. To control such generation, one of the principal mitigating actions adopted worldwide has been the alternative burning of fuels originating from renewable sources. Furthermore, it is also of great importance to reduce the consumption of petroleum and, having this objective, to increase the offer of synthetic and semisynthetic fuels.

The worldwide trend in terms of the utilisation of fuels not derived from petroleum, renewable or not, commenced with the land transport mode and has now reached with considerable strength the aeronautical industry.

According to the International Air Transport Association (IATA) world aviation is responsible for 2% of the total volume of emissions of carbon dioxide produced by man.

IATA, in its annual report ('2009 Report on Alternative Fuels'), announced that the associates thereof assume the obligation by 2017 of utilising 10% alternative fuels in the inventory thereof of aviation fuels consumed annually.

The legislation of the European Union has furthermore just brought aviation within the EU Emissions Trading Scheme (ETS) by means of Directive EC/2008/101, with a view to preparing it to satisfy the requirements of the directive.

The European Commission (EC) has drawn up a paper entitled 'Guidelines for the monitoring and reporting of aviation activity data' guiding those airlines falling within the scope of the directive to take, as from 1 Jan. 2010, a series of steps in terms of monitoring emissions of $CO_2$ and controlling consumption by aircraft operating in or overflying Europe.

IATA classifies the diverse families of fuels not derived from petroleum possessing properties similar to standard aviation kerosene (QAV) as alternative aviation fuels (Alternative Jet Fuels (AJFs)).

AJFs may be derived from biological materials as well as from coal and natural gas. The majority of AJFs may be categorised as synthetic paraffinic kerosenes (SPKs); should such SPKs be derived from biomasses other than coal or natural gas they are categorised as bioSPKs.

Synthetic hydrocarbons are synthetic fuels not restricted to the kerosene band and may be produced from coal liquefaction (Coal-to-Liquid (CTL)), from gas liquefaction (Gas-to-Liquid (GTL)), or by biomass liquefaction (Biomass-to-Liquid (BTL)) by means of the Fischer-Tropsch (FT) process. They are generically denominated XTLs or fuels produced by liquefaction of any of the aforesaid raw materials by the FT process and are considered to be variants of SPKs.

Instead of being subjected to the FT process a natural oil may be pyrolysed (thermal cracking of coal, natural gas or biomass), the oxygens thereof being removed generating a liquid fuel having properties similar to those of kerosene. These products are called hydrodeoxygenated oils (HDOs) and by virtue of the fact that they are not paraffinic they are not considered to be SPK variants.

A further common biofuel production practice is the utilisation of vegetable oils extracted from seeds, such as soya and canola. These vegetable oils are thermally cracked and subsequently chemically improved through the addition of hydrogen by means of a hydrotreatment process. The kerosene fraction of these products is called renewable hydrotreated aviation kerosene (Hydrotreated Renewable Jet (HRJ) Fuel), another variety of SPK.

Vegetable oils hydrotreated simply for the production of diesel, not usually achieving the quality necessary for the production of aviation kerosene, are called hydrotreated vegetable oils (HVOs).

There is a further category of AJFs not included in the current IATA classification, possibly because to date it has only been used to produce biodiesel and not biokerosene (bioSPK), being the category of alkyl esters of fatty acids.

The process for the production of alkyl esters of fatty acids through catalysed transesterification of oils of natural origin, already in the public domain in so far as the production of biodiesel is concerned, still requires improvement to be suitable for the production of finished aviation biokerosene.

Vacuum fractionation of hydrocarbons is a refining process utilised when it is desired to obtain lighter distilled products with minimum thermal cracking of the residual heavy fractions. It should be mentioned that none of the alternative aviation fuels cited herein has received certification from aircraft manufacturers to be used pure. All the products have been used in mixtures with conventional aviation kerosene, it being recorded that the maximum quantity utilised was a concentration of 50% by volume of a synthetic paraffinic kerosene with a conventional aviation kerosene.

That is to say, all those utilised to date have been semisynthetic aviation kerosenes and such utilisation under actual flight conditions has only become possible following the creation of specification ASTM D7566 'Standard Specification for Aviation Turbine Fuel Containing Synthesized Hydrocarbons', now adopted worldwide in the certification of these types of product.

RELATED ART

As aforesaid, not even IATA has listed in its generic classification of alternative aviation fuels the said family of chemical compounds of natural origin.

All that reported in the present state of the art relates to the utilisation of these alkyl esters of fatty acids as biodiesel or in the production of hydrocarbons by the hydrotreatment route (HVOs) directed towards other applications. This is because the products generated by these two routes do not permit the direct incorporation of an HVO into a commercial aviation kerosene (QAV-1), by virtue of the fact that such HVOs do not satisfy some important QAV-1 specifications, principally in respect of the freezing point measured by the ASTM D2386 method and which is required to be lower than −47° C. Furthermore, these processes cannot be applied to any type of natural oil or fat on pain of the final product not even falling within the QAV distillation range.

Patent document WO 2009/018390, for example, teaches a process of biodiesel production including an initial stage of vacuum distillation of particular fatty acids produced from vegetable oils, followed by a process of esterification of the predistilled fatty acids. That is to say, the document teaches a process which firstly purifies the fatty acids to subsequently convert them into esters to be used as biodiesel. Consequently, the art still requires adaptations to be capable of being employed in a process of obtainment of an aviation biokerosene starting from vegetable oils, being very much more abundant in nature than the respective fatty acids.

The objective of the present invention is the development of a process of obtainment of a BioQAV capable of converting oils of renewable origin into a product which, on addition to a conventional QAV of mineral origin, gives rise to a composition falling within the national and international specifications accepted for certification of the final product as aviation kerosene.

Hereinafter, for reasons of simplicity, aviation biokerosene will be referred to as BioQAV-100.

SUMMARY OF THE INVENTION

The present invention relates to a process of obtainment of aviation biokerosene and an aviation kerosene composition containing the aviation biokerosene thus produced. The process consists of simultaneously combining three basic conditions: raw material selection, processing conditions, and control of specific properties of the product.

In order to satisfy the requirements of the process, raw material for biodiesel production is selected from among light oils of vegetable origin rich in glycerides containing fatty acids having chains of six to fourteen carbon atoms.

The raw material selected is then subjected to a transesterification process under conditions adjusted to generate a product with acidity and total glycerine content below the maximum limits of the biodiesel specification. Following transesterification the biodiesel charge, duly 'overspecified' in terms of water content, total glycerine content and acid number, is then subjected to vacuum fractionation under controlled conditions.

The operating conditions used during the fractionation process are adjusted such that the heavy fraction retained at the bottom of the fractionation tower satisfies the specifications defined for finished biodiesel and the light fraction, being aviation biokerosene (BioQAV-100), has properties compatible with those established for aviation kerosene obtained from commercial petroleum.

Control of the vacuum fractionation processing conditions of the present invention ensures the obtainment of a product having a freezing point lower than −10° C. in the distilled light fraction, permitting utilisation thereof of up to 20% by weight in the formulation of a finished semisynthetic aviation biokerosene (BioQAV-1).

DETAILED DESCRIPTION OF THE INVENTION

In the first stage of the process for the production of BioQAV-100 a raw material of renewable origin, which may be a light vegetable oil rich in glycerides containing from six to fourteen carbon atoms in the chain of the fatty acids, selected from a group comprising, inter alia, oils of coconut, babassu, oil palm, ouricuri, or mixtures thereof in any proportion, is subjected to an adapted transesterification process based on the known processes of biodiesel production. This transesterification process may be conducted in one, two or more stages, in continuous reactors or batches.

The reaction system must be dimensioned to overspecify the biodiesel resulting from transesterification, in terms of content of mono-, di- and triglycerides, water content and principally in respect of the acid number, such that even following removal of the fraction of light esters which will comprise the BioQAV-100, the final product still satisfies biodiesel specifications. Following each reaction stage there must be a stage of separation of the glycerine phase formed. In particular, separation of the glycerine phase produced in the second stage of reaction must be as efficient as possible to minimise or avoid the use of acid for neutralisation of the biodiesel obtainment phase. This latter separation stage may be by centrifuge, coalescence systems or even gravity decantation systems designed to operate with a high efficiency of separation. Ideally, the acid number of the biodiesel prior to removal of the fraction of light esters must be lower than 0.07 mg KOH/g of sample.

The biodiesel phase, following separation of the glycerine, is sent to a purification system having the objective of removal of excess alcohol, residual catalyst, soaps and other contaminants.

The purification system may be of the washing type with demineralised water/drying, adsorption with resins or any other type of adsorbent, vacuum evaporation/distillation of the biodiesel and separation of the liquid phase containing the impurities, or a combination of these processes, including other stages such as cooling for crystallisation of impurities and filtration or centrifugation of the impurities.

In a general manner, whichever process is adopted it must reduce impurities in the charge to values below the values specified for biodiesel. This margin must be sufficient to compensate for the increase in concentration flowing from removal of the fraction of light esters. Consequently, the degree of severity of transesterification and/or purification must increase with increasing production of the BioQAV-100 fraction.

In a second stage, the biodiesel produced is sent to a particular stage of a vacuum distillation tower wherein occurs the fractionation of the alkyl esters, there being separated the fraction constituted by derivatives of fatty acids of 6 to 14 carbon atoms which leaves at the top. Part of the condensed fraction returns to the first stage of the distillation tower (top) as reflux and the remainder is collected in the BioQAV-100 tank.

The bottom product, constituted by the fraction of alkyl esters derived from fatty acids of chain containing more than 14 carbon atoms and part of the lauric esters (12 carbon atoms), leaves at the bottom of the distillation tower.

The ideal operating conditions of the distillation tower: temperature, pressure, reflux rate and number of fractionation stages, vary as a function of the raw material selected and BioQAV yield desired from the process.

The absolute pressure at the bottom of the distillation tower must be sufficiently low for the tower to operate at temperatures below conditions of degradation of the light alkyl esters, having a carbon chain containing from 6 to 14 atoms, in this manner avoiding acidification of the products. For this reason the pressure control at the top of the tower is maintained below 100 mmHg, preferably between 1 and 20 mmHg.

Temperature control throughout the distillation tower is adjusted such that fractionation specifies a top product having a freezing point lower than −10° C., preferably equal to or below −13° C.

The lower the freezing point the greater the BioQAV-100 content which may be incorporated into the QAV, however the lower the yield of BioQAV-100 from the process. This signifies that preferential esters for production of BioQAV-100 are those derived from capric, caprilic and caproic acids.

The esters of lauric acid may also be present, however at limited content, preferably below 30%, by virtue of the fact that the greater the content of esters of lauric acid in the BioQAV-100 the higher the freezing point. In this manner, the design of the vacuum distillation tower must include a number of fractionation stages to minimise losses of esters derived from capric acid from the bottom of the tower.

Fractionation must be executed preferably in fractionation columns capable of operating continuously, promoting low dwell times of the charge in the column. Alternatively, batch operations may be used, always provided that dwell time is minimised.

Should the acidity of the bottom product not fall within biodiesel specifications as a result of degradation during fractionation or because the process of transesterification and purification does not achieve the 'overspecification' necessary to compensate the effect of concentration flowing from the removal of the light fraction, the product is sent to a neutralisation section.

In the neutralisation section the product is mixed with an alkaline solution, preferentially a solution of sodium hydroxide having a concentration which may range from 5% w/w to 50% w/w, to reduce the acid number to below 0.5 mg KOH/g or that value established by the regional specification required. Alternatively, the product may be sent to a mixing reactor, at a temperature of between 20° C. and 100° C. having a dwell time of between 1 and 30 minutes, or caustic washing tower or alkaline fixed bed reactor. The neutralised product subsequently continues to one or more stages of washing with demineralised water, preferentially countercurrent, at a temperature of between 20° C. and 100° C., followed by decantation, for removal of soaps and excess alkaline agent used in neutralisation. Alternatively, the neutralised product may pass through a sludge separator, gravimetric or centrifugal, prior to such washing, for removal of the sludge from neutralisation, minimising consumption of demineralised water. The quantity of water and number of washing/neutralisation stages is dimensioned to reduce sodium content added to potassium content to the value established by the biodiesel specification, normally below 5 ppm. The product then continues to the biodiesel dryer where evaporation and removal of water takes place at a temperature of between 60° C. and 120° C. under vacuum (absolute pressure between 200 and 1 mmHg).

The ideal conditions of drying temperature and pressure must be established in accordance with the type of vegetable oil used as a charge such as to have no loss of BioQAV through evaporation. Alternatively, following separation of the neutralisation sludge, residual soaps may be adsorbed with silica gel followed by drying and filtration of the product on a diatomaceous earth filter or equivalent.

As a further alternative, residual soaps may also be adsorbed on an ion-exchange resin bed.

In the same manner, should the product from the top of the vacuum distillation present an acidity incompatible with the final value of 0.015 mg KOH/g in the mixture of BioQAV-100 with QAV, the top product must be subjected to the same type of neutralisation described previously for the bottom product.

In oils having high lauric acid content, such as oils of babassu, oil palm, ouricuri, the present invention includes the alternative of production of an intermediate stream, concentrated in lauric acid ester, by means of the introduction into the distillation column of an intermediate draw-off plate. The production of lauric acid esters, depending on plant logistics and market conditions, adds value to the products, contributing to improvement in the profitability of the process.

EXAMPLE

The example provided below has the objective of illustrating one form of embodiment of the invention together with proving the possible practical applicability thereof, not constituting any form of limitation of the invention.

A charge of babassu oil is utilised as raw material of the transesterification stage. This oil is transferred to a mixing reactor together with methanol and an alkaline catalyst, which may be selected from among sodium or potassium ethoxide, sodium or potassium methoxide, sodium or potassium hydroxide. The mixture is set to react during 60 minutes at a temperature of 60° C. At the end of the reaction period the mixture is transferred to a decanter wherein it remains decanting for two hours. At the end of the decantation period the heavy phase, rich in glycerine, is removed through the bottom of the decanter. Then the light phase, rich in biodiesel, is transferred back to the reactor together with a fresh charge of methanol and alkaline catalyst. The reaction and decantation procedure is repeated a further time, generating a light phase of crude biodiesel. This biodiesel is transferred to a washing vessel together with a charge of demineralised water in a proportion which may lie in the range from 5 to 50 parts of biodiesel per part of water. The stirrer of the washing vessel is activated for 5 minutes to proceed to extraction of contaminants, principally soaps, excess methanol and residual catalyst. After 5 minutes the mixture is transferred to a decanter wherein it remains decanting for two hours. At the end of the decantation period the aqueous phase is removed through the bottom of the decanter. Then the biodiesel is transferred back to the washing vessel together with a further charge of demineralised water. The washing procedure is repeated a further time, generating a light phase of damp biodiesel. The aqueous phase of the second wash is retained to be used as water in the first washing stage of the biodiesel produced in the following batch. The damp biodiesel is then transferred to a dryer, wherein it is heated to 80° C. under an absolute pressure lower than 730 mmHg to reduce the water content to a value lower than 500 ppm.

The transesterification procedure of the babassu oil is repeated numerous times until sufficient volume is accumulated for processing in the vacuum distillation system. However, there is no filtration stage to improve the biodiesel, for which reason the product does not satisfy the national specification in terms of contaminants. Furthermore, due to the time awaiting commencement of the vacuum distillation stage the biodiesel adsorbs humidity from the air. This being the case, with the exception of the contamination and humidity items, the methyl esters produced in the transesterification stage fall within the Brazilian biodiesel specification (ANP Resolution no. 7, of 19 Mar. 2008), as shown by the results provided in Table 1 below.

The biodiesel produced is subjected to a series of experimental laboratory distillations to define the conditions adopted in an experimental run in a semi-industrial vacuum fractionation unit, also conventional.

The temperature of the charge vessel is approximately 50° C. and the preheater raises the temperature of the biodiesel to the range from 125° C. to 135° C. with the objective of contributing to the separation of the fractions at the top of the fractionation column.

The unit operates under a vacuum of 1 mmHg to 10 mmHg and the temperature at the top of the column is maintained in the range from 80° C. to 110° C.

The rectification column of the unit utilised, which possesses from 14 to 18 equilibrium stages constituted by structured packing, receives heat by means of a set of resistances located in the bottom thereof (reboiler) which bring the charge up to a temperature of the order of 170° C. The unit is operated under vacuum to prevent very high temperatures in the bottom section, in this manner minimising degradation of the product with increase in acidity.

Depending on the stability of the operation of the fractionation unit, refluxing may lie in the range from 5:1 to 7:1 in terms of volume of liquid returning to the column. Refluxing is normally controlled by manipulation of the opening of the control valve which adjusts the flow of biokerosene required for return to the fractionation column.

TABLE 1

| PROPERTY | | ANP Res. No. 7 | Biodiesel charge |
|---|---|---|---|
| Aspect (visual) | | LII | Clear and limpid |
| Volatility | Density at 15° C. (ASTM D4052), kg/m$^3$ | 850 to 890 | 871.1 |
| | Flash point (ASTM D93), ° C. | 100 min. | 115.0 |
| Fluidity | Viscosity at 40° C. (ASTM D445), cSt | 3.0 to 6.0 | 2.914 |
| | Cold filter plugging point (ASTM D6371), ° C. | (a) | −7 |
| Composition | Ester content (CENPES), % weight | 96.5 min. | 98.74 |
| | Total sulphur (ASTM D5453), mg/kg | 50 max. | 5.4 |
| Combustion | Carbon residue, 100% distilled (ASTM D4530), % weight | 0.05 max. | (b) |
| | Cetane number (ASTM D6890) | record | (b) |
| | Sulphated ash (ASTM D874), % weight | 0.02 max. | 0.0003 |
| Corrosion | Copper corrosion, 3 h, 50° C. (ASTM D130) | 1 max. | 1A |
| Contaminants | Water and sediment (ASTM D2709), % vol. | — | 0.10 |
| | Water by Karl Fisher (ASTM D6304), mg/kg | 500 | 550 |
| | Sodium + Potassium (EN 14108/14109), mg/kg | 5 max. | <1.0; <1.0 |
| | Calcium + Magnesium (EN 14538), mg/kg | 5 max. | <1.0; <1.0 |
| | Phosphorus (Plasma - CENPES), mg/kg | 10 max. | <1.0 |
| | Free glycerine (ASTM D6584), % weight | 0.02 max. | <0.01 |
| | Total glycerine (modified AOCS), % weight | 0.25 max. | 0.134 |
| | Monoglycerides (ASTM D6584), % weight | record | 0.58 |
| | Diglycerides (ASTM D6584), % weight | record | 0.11 |
| | Triglycerides (ASTM D6584), % weight | record | 0.06 |
| | Methanol or ethanol (CENPES), % weight | 0.2 max. | <0.01 |
| | Total contamination (EN 12662), mg/kg | 24 max. | 72.6 |
| Acid number (ASTM D664), mg KOH/g | | 0.5 max. | 0.06 |
| Iodine value (EN 14111), g/100 g | | record | 20 |
| Oxidation stability at 110° C. (EN 14112), h | | 6 min. | 18.7 |

LII—limpid and impurity free;
(a) the diesel oil/biodiesel mixture utilised must satisfy the cold filter plugging point limits established in the ANP automotive diesel oil specification in force.
(b) the results obtained lie outside the range covered by the method.

The bottom product after leaving the distillation column is immediately cooled, in the case of the experiment to 25° C. to 30° C.

Both the top product collecting vessel and that of the bottom operate under atmospheric pressure.

The top product from the distillation tower must, preferentially, possess a freezing point lower than −10° C., preferentially below −13° C. Following adjustments undertaken during the preoperational phase of the unit the operating conditions shown in Table 2 are used.

TABLE 2

| Run 15 | Operating Conditions |
|---|---|
| Charge | Babassu Biodiesel |
| Pressure, mmHg | 10 |
| Temperature at the top of the fractionation column, ° C. | 80 to 120 |
| Temperature at the bottom of fractionation column, ° C. | 161 to 165 |
| Number of equilibrium stages | 14 to 18 |
| Reflux rate | from 5:1 to 7:1 |

In the semi-industrial unit a babassu biodiesel is charged into the charging vessel of the unit. The charging pump operates at an average rate of 2 l/h. The temperature of the biodiesel charge in the charging vessel is approximately 50° C. and in the preheater the temperature is maintained in the range from 125° C. to 135° C. with the objective of contributing to the separation of the fractions at the top of the fractionation column.

The unit operates under a vacuum of 10 mmHg and the temperature at the top of the column is strictly controlled in the range from 80° C. to 120° C. through external refluxing of the biokerosene, which varies within a range from 5:1 to 7:1.

The temperature of the bottom of the fractionation column is maintained at approximately 165° C. The level of the charge at the bottom of the fractionation column is maintained stable by means of a system of communicating vessels and the bottom collecting pump is always maintained submerged.

The 'heavy' biodiesel is removed from the bottom product collecting vessel at ambient temperature. Both the top product collecting vessel and that of the bottom operate under atmospheric pressure.

The results obtained during monitoring of the production of the aviation biokerosene are shown in Table 3.

TABLE 3

| TEST | RESULT |
|---|---|
| Freezing point (ASTM D2386), ° C. | −18 |
| Acid number (ASTM D664), mgKOH/g | 0.024 |
| Density at 20° C./4° C. (ASTM D4052), kg/m$^3$ | 0.8735 |

Tables 4, 5 and 6 below show respectively the results obtained for the 'heavy' biodiesel, for a commercial aviation kerosene (QAV-1) and for a composition of semisynthetic aviation biokerosene (BioQAV-10) formulated with 10% by weight pure aviation biokerosene (BioQAV-100) and 90% QAV-1.

The results obtained in Tables 4, 5 and 6 indicate that the 'heavy' biodiesel, following small adjustments, may be marketed directly from the production unit and that the BioQAV-10 produced in conformity with the conditions provided in the present invention is in a condition for submission for international certifications governing the marketing of semisynthetic aviation kerosenes, today being the general criterion of utilisation of these types of fuel in the world.

TABLE 4

| TEST | ANP Res. no. 7 | Heavy biodiesel |
|---|---|---|
| Density at 15° C. (ASTM D4052), kg/m³ | 850 to 890 | 871.1 |
| Viscosity at 40° C. (ASTM D445), cSt | 3.0 to 6.0 | 3.246 |
| Free glycerine (ASTM D6584), % weight | 0.02 max. | 0.01 |
| Total glycerine (modified AOCS), % weight | 0.25 max. | 0.389 |
| Oxidation stability at 110° C. (EN 14112), h | 6 min. | 6.6 |

TABLE 5

| TEST | ASTM Spec. D1655 | QAV-1 |
|---|---|---|
| Appearance (ASTM D4176) | LIMS (1) | LIMS |
| Saybolt Colour (ASTM D156) | | 28 |
| Particulate contamination (ASTM D5452), mg/l | 1.0 max. | 0.0 |
| Total acid number (ASTM D3242), mg KOH/g | 0.015 max. | 0.01 |
| Aromatics (ASTM D1319), % volume | 25.0 max. | 18.7 |
| Total sulphur (ASTM D2622), % weight | 0.30 max. | 0.005 |
| Mercaptan sulphur (ASTM D3227), mg/kg | 30 max. | <2 |
| Distillation temperature (ASTM D86) | | |
| Initial boiling point, ° C. | | 159 |
| 10% recovered, ° C. | 205 max. | 173.3 |
| 50% recovered, ° C. | report | 205.5 |
| 90% recovered, ° C. | report | 251.9 |
| Final boiling point, ° C. | 300 max. | 284.2 |
| Residue, % volume | 1.5 max. | 1.0 |
| Losses, % volume | 1.5 max. | 0.8 |
| Density at 15° C. (ASTM D4052), kg/m³ | 775 to 840 | 813.6 |
| Flash point (ASTM D56), ° C. | 40 min. | 46.5 |
| Kinematic viscosity at −20° C. (ASTM D445), cSt | 8.000 max. | 4.676 |
| Freezing point (ASTM D2386), ° C. | −47 max. | 49.5 |
| Lower calorific power (ASTM D4809), MJ/kg | 42.8 min. | 42.9 |
| Flash point (ASTM D1322), mm | 25.0 min. | 20.0 |
| Flash point (ASTM D1322), mm e | 19 min. | 20.0 |
| Naphthalenes (ASTM D1840), % volume | 3.00 max. | 2.0 |
| Silver corrosion, 4 h at 50° C. (ASTM D4814-04b) | 1 max. | 0 |
| Copper corrosion, 2 h at 100° C. (ASTM D130) | 1 max. | 1B |
| JFTOT (ASTM D3241), ΔP at 260° C., mmHg | 25.0 max. | 0.0 |
| deposit in tube (visual) | <3 max. (2) | <1 |
| gum (ASTM D381), mg/100 ml | 7 max. | 0.5 |
| Water tolerance (ASTM D1094) | 1b max. | 1b |
| WSIM (fuel without SDA) (ASTM D3848) | 85 max. | 85 |
| Metal content (ASTM D3605), µg/kg | | |
| Na | — | 43 |
| Fe | — | 26 |
| Zn | — | 9.4 |
| Cu | — | <5 |
| Pb | — | <5 |
| Electrical conductivity (ASTM D2624), pS/m | 50-450 (3) | 19 |
| BOCLE lubricity (ASTM D5001) | 0.85 max. (4) | 0.60 |

Where:
(1) clear and sparkling and visually free of water and insoluble material at ambient temperature;
(2) the deposit must not have a deposit of abnormal colour or pav colour;
(3) limits required at the premises, time and temperature of delivery to the purchaser, should the fuel contain electrical charge dissipation additive;
(4) the lubricity control is solely applied to fuels containing more than 95% hydroprocessed fraction, whereof this fraction a minimum of 20% has been severely hydroprocessed. The limit is solely applicable in production.

TABLE 6

| TEST | ASTM Spec. D1655 | BioQA V-10 |
|---|---|---|
| Appearance (ASTM D4176) | LIMS (1) | LIMS |
| Saybolt Colour (ASTM D156) | | 21 |
| Particulate contamination (ASTM D5452), mg/l | 1.0 max. | 0.005 |
| Renewables content (infrared spectrometry), % weight | — | 10 |
| Total acid number (ASTM D3242), mg KOH/g | 0.015 max. | 0.011 |
| Aromatics (ASTM D1319), % volume | 25.0 max. | 18.7 |
| Total sulphur (ASTM D2622), % weight | 0.30 max. | 0.00 |
| Mercaptan sulphur (ASTM D3227), mg/kg | 30 max. | <2 |
| Distillation temperature (ASTM D86) | | |
| Initial boiling point, ° C. | report | 159 |
| 10% recovered, ° C. | 205 max. | 175 |
| 50% recovered, ° C. | report | 205 |
| 90% recovered, ° C. | report | 252 |
| Final boiling point, ° C. | 300 max. | 282 |
| Residue, % volume | 1.5 max. | 1.3 |
| Losses, % volume | 1.5 max. | 0.0 |
| Density at 15° C. (ASTM D4052), kg/m³ | 775 to 840 | 819.2 |
| Flash point (ASTM D56), ° C. | 40 min. | 47 |
| Kinematic viscosity at −20° C. (ASTM D445), cSt | 8.000 max. | 4.749 |
| Freezing point (ASTM D2386), ° C. | −47 max. | −47 |
| Lower calorific power (ASTM D4809), MJ/kg | 42.8 min. | 41.6 |
| Flash point (ASTM D1322), mm | 25.0 min. | 22.0 |
| Flash point (ASTM D1322), mm e | 19 min. | 22.0 |
| Naphthalenes (ASTM D1840), % volume | 3.00 max. | 1.43 |
| Silver corrosion, 4 h at 50° C. (ASTM D4814-04b) | 1 max. | 0 |
| Copper corrosion, 2 h at 100° C. (ASTM D130) | 1 max. | 1B |
| JFTOT (ASTM D3241), ΔP at 260° C., mmHg | 25.0 max. | 0.0 |
| deposit in tube (visual) | <3 max. (2) | <1 |
| gum (ASTM D381), mg/100 ml | 7 max. | 0.5 |
| Water tolerance (ASTM D1094) | 1b Max. | 1b |
| WSIM (fuel without SDA) (ASTM D3848) | 85 max. | 85 |
| Metal content (ASTM D3605), µg/kg | | |
| Na | — | 43 |
| Fe | — | 26 |
| Zn | — | 9.4 |
| Cu | — | <5 |
| Pb | — | <5 |
| Electrical conductivity (ASTM D2624), pS/m | 50-450 (3) | 19 |
| BOCLE lubricity (ASTM D5001) | 0.85 max. (4) | 0.49 |

Where:
(1) clear and sparkling and visually free of water and insoluble material at ambient temperature;
(2) the deposit must not have a deposit of abnormal colour or pav colour;
(3) limits required at the premises, time and temperature of delivery to the purchaser, should the fuel contain electrical charge dissipation additive;
(4) the lubricity control is solely applied to fuels containing more than 95% hydroprocessed fraction, whereof this fraction a minimum of 20% has been severely hydroprocessed. The limit is solely applicable in production.

The BioQAV-10 produced in this process is a product ready for testing and approval as what is considered, in the international jargon, a product fit for purpose, that is to say satisfying the objective for which it is destined and becoming an adequate and sufficient substitute (drop-in) for use in commercial aviation.

The invention claimed is:
1. A process for the production of aviation bio-kerosene, characterized in that it simultaneously combines three basic conditions: raw material selection, processing conditions, and control of specific properties of the product, comprising the following stages:
   a) subjecting a raw material of renewable origin comprising glycerides having from six to fourteen carbon atoms in a chain of the fatty acids to a transesterification process under conditions adjusted to generate an overspecified biodiesel charge with an acid number below 0.07 mg KOH/g and a total glycerine content below the maximum limits of the biodiesel specification;

b) feeding the overspecified biodiesel charge to a vacuum distillation tower operating under vacuum from 1 mmHg to 100 mmHg, wherein a temperature at the top of the distillation tower is maintained in the range of from 80° C. to 110° C., such that an aviation biokerosene fraction is removed from the top of the distillation tower, and a biodiesel fraction having an acid number below 0.5 mg KOH/g is removed from the bottom of the vacuum distillation tower; and c) controlling the freezing point value of the bio-kerosene removed from the top of the distillation tower such that it is lower than −10° C.

2. The process for the production of aviation biokerosene according to claim 1, characterized in that the biodiesel removed from the bottom of the vacuum distillation tower possesses properties to permit the marketing thereof as such.

3. The process for the production of aviation biokerosene according to claim 1, characterized in that the product from the top of the distillation column may be added to a commercial aviation kerosene in a proportion of up to 20% by weight.

4. The process for the production of aviation biokerosene according to claim 1, wherein the raw material of renewable origin is a light vegetable oil selected from the group consisting of oils of coconut, babassu, oil palm, ouricuri, and mixtures thereof in any proportion.

5. The process for the production of aviation biokerosene according to claim 1, characterized in that the freezing point value of the bio-kerosene removed from the top of the distillation tower is controlled to be lower than −13° C.

6. The process for the production of aviation biokerosene according to claim 1, characterized in that the distillation tower comprises 14 to 18 stages.

7. The process for the production of aviation biokerosene according to claim 1, characterized in that the distillation tower is operating under a vacuum of from 1 mmHg to 20 mmHg.

* * * * *